United States Patent [19]

Schwarz

[11] Patent Number: 4,804,753

[45] Date of Patent: Feb. 14, 1989

[54] PROCESS FOR THE PREPARATION OF SCHIFF'S BASES

[75] Inventor: Hans-Helmut Schwarz, Krefeld, Fed. Rep. of Germany

[73] Assignee: Bayer Aktiengesellschaft, Leverkusen, Fed. Rep. of Germany

[21] Appl. No.: 817,205

[22] Filed: Jan. 8, 1986

[30] Foreign Application Priority Data

Jan. 23, 1985 [DE] Fed. Rep. of Germany ....... 3502105

[51] Int. Cl.$^4$ ................. C07D 225/02; C07D 223/02; C07D 211/70; C07D 207/20

[52] U.S. Cl. .................................... 540/450; 540/609; 548/565; 546/329

[58] Field of Search ................ 540/609, 450; 548/565; 546/329

[56] References Cited

U.S. PATENT DOCUMENTS 3,518,252  6/1970  Izawa et al. .................... 540/609 X
3,940,409  2/1976  Waldbillig ........................... 548/141

FOREIGN PATENT DOCUMENTS 1420044  12/1972  Fed. Rep. of Germany ...... 540/609
2303348  8/1973   Fed. Rep. of Germany .
44-24662  11/1969  Japan ................................... 540/609
44-24661  11/1969  Japan ................................... 540/609
50-64268  5/1975   Japan ................................... 540/609
54-125654 9/1979   Japan ................................... 540/609
922275    3/1963   United Kingdom .
1127117   9/1968   United Kingdom .

Primary Examiner—Anton H. Sutto
Assistant Examiner—William A. Teoli, Jr.

Attorney, Agent, or Firm—Sprung Horn Kramer & Woods

[57] ABSTRACT

A process for the preparation of Schiff's bases which contain amino groups, of the formula

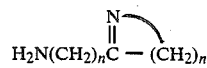

wherein
n is 3 to 12, by reacting cyclic lactams of the formula

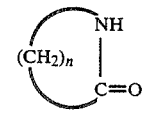

wherein
n is 3 to 12, or of their ring-opened polymers of the formula

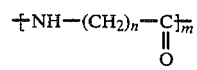

wherein
n is 3 to 12 and
m is 1 to 100,000, with inorganic bases at elevated temperature, the reaction being carried out in the presence of inert, high-boiling suspending agents.

13 Claims, No Drawings

PROCESS FOR THE PREPARATION OF SCHIFF'S BASES

BACKGROUND OF THE INVENTION

It is known to prepare Schiff's bases which contain amino groups by heating cyclic lactams, or their ring-opened polymers, such as δ-valerolactam, ε-caprolactam, n-capryllactam, nylon-4, nylon-6 or nylon-8, at temperatures below 260° C. in the presence of an alkaline earth metal hydroxide, followed by heating the reaction mixture to at least 300° C. before removal of the Schiff's bases by distillation.

According to the processes described in DE-OS (German Published Specification) No. 1,420,044 and the Japanese Application Nos. 150,832, 42,088/66, 41,766/66 and in DE-OS (German Published Specification) No. 2,303,348, cyclic lactams, or polyamides which are obtainable from the cyclic lactams by polycondensation, are heated with bases, principally calcium oxide, without any solvent to temperatures in the range from 250° to 500° C., and the volatile fractions are removed by distillation.

The carrying out of this reaction is associated with considerable difficulties, even on the laboratory scale, because the reaction mixture is transformed during the reaction into a solid, hard mas, from which the volatile fractions have to be removed by distillation. This means that stirred vessels and similar reactors are unsuitable for carrying out this reaction. Only elaborate apparatus, such as kneaders, is suitable for this purpose.

A modification of this preparation method is described in French Pat. No. 1,475,526. According to this patent specification, the reaction between the cyclic lactams and the alkaline earth oxides is carried out in a fluidized bed. This process represents a very elaborate technique which is characterized by high investment costs and difficulty of operation.

SUMMARY OF THE INVENTION

A straightforward process has now been found for the preparation of Schiff's bases which contain amino groups, of the formula

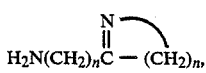
(I)

in which
n denotes 3 to 12,
by reaction of cyclic lactams of the formula

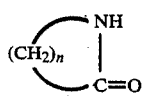
(II)

with the abovementioned meaning for n,
or their ring-opened polymers of the formula

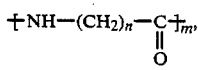
(III)

in which
n has the abovementioned meaning, and
m represents integers from 1 to 100,000, with inorganic bases at elevated temperature, which is characterized in that the reaction is carried out in the presence of inert, high-boiling, suspending agents.

DETAILED DESCRIPTION OF THE INVENTION

The cyclic lactams of the formula (II) which are preferably used in the process according to the invention ar those with $n=4$ to 12. Examples of cyclic lactams which may be mentioned are: δ-valerolactam, ε-caprolactam, n-capryllactam and laurolactam, preferably ε-caprolactam.

The polymers of the formula (III) which are preferably used in the process according to the invention are those in which n represents 4 to 10 and m represents 100 to 400. Examples which may be mentioned are polyamides, such as nylon-4, nylon-6 and nylon-8, preferably nylon-6.

The substances suitable for the suspension of the participants in the reaction must be chemically inert towards the reactants used, be in a liquid state at the reaction temperatures, and have a boiling point which is sufficiently high that only small fractions distil out with the Schiff's bases and the starting materials.

Examples of suitable suspending agents are high-boiling aliphatic and aromatic hydrocarbons or their mixtures, high-boiling polymeric hydrocarbons and high-boiling mineral oils, such as fuel oils, and their distillation residues.

High-boiling mineral oils are preferably used as the inert suspending agents in the process according to the invention.

High-boiling mineral oils are to be understood to be high-boiling refinery products having a boiling point $\geq 250°$ C., such as gas oil, vacuum gas oil, heavy fuel oil, technical white oil, molten paraffin wax or aromatic hydrocarbon oil. Vacuum gas oil with a boiling point above 300° C., in particular with a boiling range of 350° C. to 500° C., is advantageously used.

In general, the process according to the invention is carried out in such a manner that the cyclic lactam or its ring-opened polymer, the inorganic base and the suspending agent are introduced into a stirred flask or stirred vessel, which with larger units should have a wall-sweeping stirrer. The Schiff's base which is formed is removed by distillation, where appropriate in vacuo, by heating the reaction mixture to about 270° to 400° C., preferably 300° to 360° C.

The inorganic base which is particularly preferably used in the process according to the invention is calcium oxide. However, it is also possible to use other alkaline earth oxides and/or hydroxides as well as alkali metal oxides and/or hydroxides, such as sodium hydroxide, potassium hydroxide, strontium and/or barium oxide, as well as lithium carbonate, in the process according to the invention.

The ratio of the amount of the cyclic lactam, or its ring-opened polymer, on the one hand to the inorganic bases which are to be used, on the other hand, can vary within wide limits. However, it is advisable to use at least 0.5 mole of an inorganic base (for example: CaO) for each 1 mole of the lactam which is to be used, or its ring-opened polymer, since with smaller amounts of inorganic base the yields of Schiff's bases obtained are inadequate. Preferably, 0.55 to 0.95 mole of an inorganic base (for example: CaO) is used for each 1 mole of the cyclic lactam which is used, or its ring-opened polymer, in the process according to the invention.

The amount of inert, high-boiling suspending agent should not be less than 25% by weight relative to the mixture of all the components used, because then, under certain circumstances, the mixture cannot be stirred at all states of the reaction. Preferably, 30 to 70% by weight of the high-boiling suspending agent, relative to the mixture of all the components used, are used in the process according to the invention. If portions of the suspending agent distil out during the reaction, then it is possible subsequently also to meter suspending agent in during the reaction in order to maintain a stirrable state.

It may be advantageous for the process according to the invention for the heating process to be slowed down in the suitable temperature range in order to allow polycondensation of the lactams. When, for example, ε-caprolactam is used, this temperature range is about 220° to 250° C.

The use of inert, high-boiling suspending agents in the process according to the invention permits the preparation in an industrially straightforward and economic manner of Schiff's bases which contain amino groups. The use of suspending agents results in a stirrable reaction mixture being obtained, which can be processed in normal stirred vessels in all stages of the reaction, without the occurrence of interfering agglomeration of the solid participants in the reaction.

Re-use of the suspending agents is possible after removal of inorganic constituents, for example by filtration or centrifugation. A great purifying effect is achieved when the suspending agent, principally mineral oils, is treated with aqueous mineral acids, which dissolve the carbonates and bases as well as basic organic substances, and the aqueous phase which results from this is removed. Residues of acids can then be removed from the suspending agent by a wash with water or alkali. Precipitated solids can be removed by filtration.

Since fuel oils or vacuum gas oil are available at reasonable cost, these suspending agents will, as a rule, be burnt as fuel, and the reaction will be charged with fresh mineral oil.

The examples which follow are intended to illustrate the process according to the invention but without restricting it to these examples.

EXAMPLE 1

1412 g of caprolactam, 403.5 g of CaO and 605 g of paraffin oil were heated in a stirred flask to 315° C. over the course of 3.2 h. At this time, the contents of the flask were adjusted to a pressure of 708 mbar. The 7-(5-aminopentyl)-3,4,5,6-tetrahydro-2H-acepine which was formed began to distil out. The vacuum was gradually reduced to 175 mbar during the subsequent two hours. Once the amount of distillate which had been produced was 700 ml, 878 g of paraffin oil were pumped into the stirred flask.

A two-phase distillate was produced during this process. It consisted of 43 g of an upper paraffin phase. The lower phase (1010 g) contained, according to analysis, 71.9% of acepine and 10.3% of caprolactam. This corresponded to a lactam conversion of 92.6%, an acepine selectivity of 68.9%, and a yield of 63.8% based on caprolactam.

EXAMPLE 2

182.8 g of 2-pyrrolidone, 69.4 g of CaO and 260 g of paraffin oil were heated in a stirred flask at 220° C. for 1 h. The temperature was then increased to 310° to 320°, and distillation was carried out under 25 mbar. The distillate consisted of two phases. The upper phase (68.6 g) consisted of paraffin oil. The lower phase (91.43 g) contained, according to GC analysis, 36.9 g of unreacted pyrrolidone and 44.3 g of 3,4-dihydro-2H-pyrrole-5-propanamine. This corresponded to a pyrrolidone conversion of 79.7% and a yield of 40.9%.

EXAMPLE 3

429.4 g of polycaprolactam granules (m=100–400) (Durethan BK ® of Bayer AG), 112 g of CaO and 260 g of technical white oil (Catenex oil$^{P941}$ ® of Shell AG) were reacted by the procedure of Example 1. A two-phase distillate which consisted of 196.5 g of a paraffin phase and 341.3 g of an azepine phase resulted. 245.5 g of 7-(5-amino pentyl)-3,4,5,6-tetrahydro-2H-azepine and 73.5 g of lactam were determined by analysis to be in the mixture. This corresponded to a polyamide conversion of 82.9% and an azepine selectivity of 85.6% and an azepine yield based on polyamide of 70.1%.

EXAMPLE 4

243 g of caprolactam, 104.1 g of CaO and 260 g of heavy fuel oil were reacted in accordance with the procedure of Example 2. 280.3 g of a distillate were obtained, and this contained, according to GC(=gas liquid chromatography) analysis, 128.1 g of 7-(5-aminopentyl)-3,4,5,6-tetrahydro-2H-azepine and 36 g of caprolactam. This corresponded to a lactam conversion of 85.2% and an azepine yield of 77.2%.

It will be appreciated that the instant specification and claims are set forth by way of illustration and not limitation, and that various modifications and changes may be made without departure from the spirit and scope of the present invention.

What is claimed is:

1. In a process for the preparation of Schiff's bases of the formula

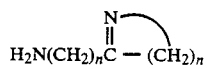

wherein
n is 3 to 12,
by reacting cyclic lactams of the formula

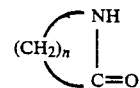

wherein
n is 3 to 12,
on their ring-opened polymers of the formula

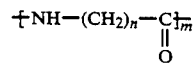

wherein
n is 3 to 12 and
m is 1 to 100,000,
with an inorganic base at an elevated temperature, wherein the improvement comprises the reaction being carried out in the presence of inert, high-boiling suspending agents selected from the group consisting of high-boiling aliphatic hydrocarbons, high-boiling aromatic hydrocarbons, mixtures of said aliphatic and aromatic hydrocarbons, high-boiling polymeric hydrocarbons and high-boiling mineral oil, wherein the amount of the suspending agent is not less than 25% by weight relative to the mixture of all reaction components, to result in a stirrable reaction mixture.

2. A process according to claim 1, wherein the inert high-boiling suspending agent is a high-boiling mineral oil.

3. A process according to claim 2, wherein the high-boiling mineral oil is an oil having a boiling point $\geq 250°$ C. selected from the group consisting of gas oil, vacuum gas oil, heavy fuel oil, technical white oil, molten paraffin wax and aromatic hydrocarbon oil.

4. A process according to claim 1, wherein the inert high-boiling suspending agent is a vacuum gas oil which has a boiling range of 350° to 500° C.

5. A process according to claim 1, wherein the amount of the inert, high-boiling suspending agent is 30 to 70% by weight relative to the mixture of all reaction components.

6. A process according to claim 1, wherein the inorganic base is selected from the group consisting of alkaline earth oxides, alkaline earth hydroxides, alkali metal oxides and alkali metal hydroxides.

7. A process according to claim 1, wherein the inorganic base is calcium oxide.

8. A process according to claim 1, wherein n is 4 to 12.

9. A process according to claim 1, wherein the cyclic lactam is selected from the group consisting of δ-valerolactam, ε-caprolactam, n-capryllactam and laurolactam.

10. A process according to claim 1, wherein the cyclic lactam is ε-caprolactam.

11. A process according to claim 1, wherein m is 100 to 400.

12. A process according to claim 1, wherein the polymer is selected from the group consisting of nylon-4, nylon-6 and nylon-8.

13. A process according to claim 1, wherein 0.55 to 0.95 moles of the inorganic base are used per 1 mole of the cyclic lactam.

* * * * *